United States Patent [19]
Solar

[11] Patent Number: 5,810,838
[45] Date of Patent: Sep. 22, 1998

[54] HYDRAULIC METHOD AND APPARATUS FOR UNIFORM RADIAL COMPRESSION AND CATHETER MOUNTING OF RADIALLY EXPANDABLE INTRALUMINAL STENTS AND STENTED GRAFTS

[76] Inventor: Ronald J. Solar, 12495 Figtree St., San Diego, Calif. 92131

[21] Appl. No.: 816,259

[22] Filed: Mar. 13, 1997

[51] Int. Cl.$^6$ ...................................................... A61F 11/00
[52] U.S. Cl. ........................... 606/108; 606/198; 128/898
[58] Field of Search ................................... 606/108, 198, 606/200, 202, 203, 192, 194; 128/898

[56] References Cited

U.S. PATENT DOCUMENTS 5,626,604  5/1997  Cottone, Jr. ............................... 606/108
5,630,830  5/1997  Verbeek .................................... 606/108

*Primary Examiner*—Michael Buiz
*Assistant Examiner*—Kevin Truong
*Attorney, Agent, or Firm*—Sereboff & Buyan

[57] ABSTRACT

An apparatus for mounting a radially expandable intraluminal stent or stented graft onto a delivery catheter. The apparatus comprises a hollow housing defining an interior chamber and a fluid port which communicates with the interior chamber. Disposed within the interior chamber of the housing is a collapsible, resilient tubular sleeve which is sized to receive a portion of the delivery catheter having the stent or stented graft positioned thereupon. The sleeve includes an open end which communicates with the exterior of the housing. The pressurization of the interior chamber of the housing via the fluid port facilitates the uniform radial compression of the sleeve, with the depressurization of the housing via the fluid port causing the sleeve to resiliently return to an uncompressed state.

11 Claims, 1 Drawing Sheet

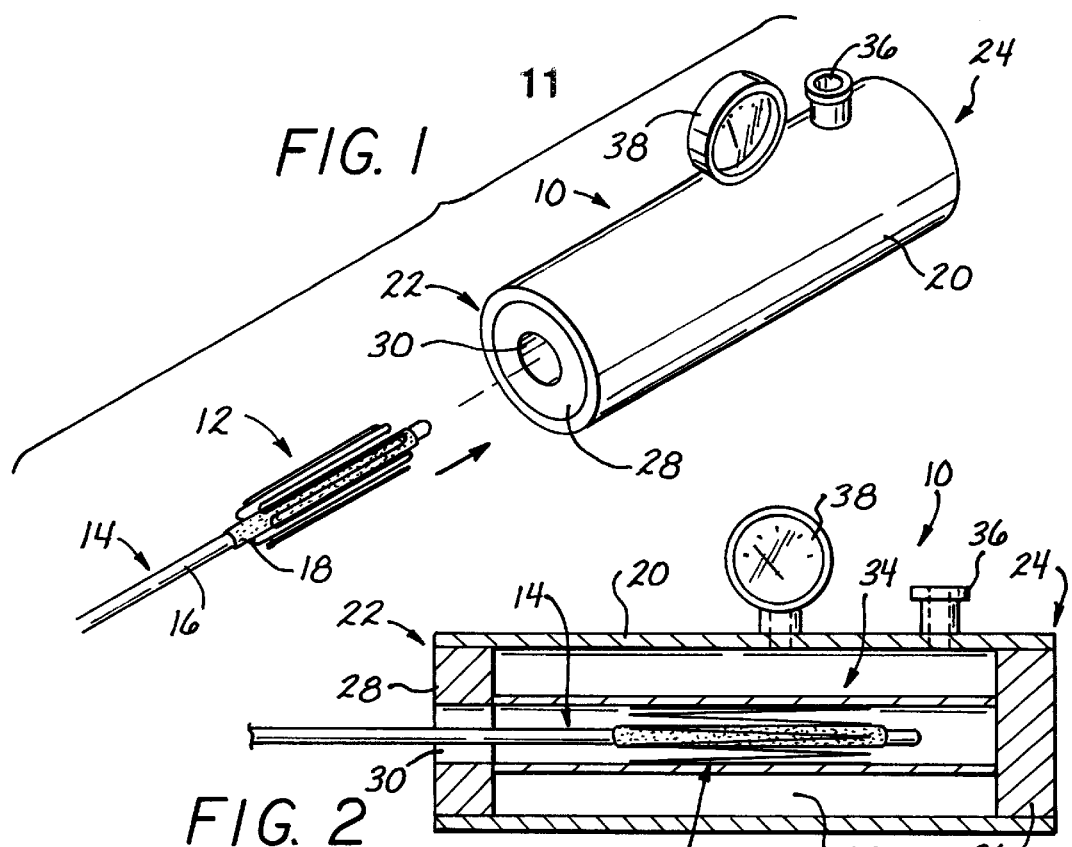

HYDRAULIC METHOD AND APPARATUS FOR UNIFORM RADIAL COMPRESSION AND CATHETER MOUNTING OF RADIALLY EXPANDABLE INTRALUMINAL STENTS AND STENTED GRAFTS

FIELD OF THE INVENTION

The present invention pertains generally to medical devices, and more particularly to an apparatus and method for mounting a stent or stented graft onto a delivery catheter through the use of hydraulics to facilitate the uniform radial compression of the stent or stented graft.

BACKGROUND OF THE INVENTION

The term "stent" is generally used to describe endoprothstetic medical devices which are implanted in anatomical passageways (e.g., blood vessels, gastrointestinal tract, genitourinary tract, endocrine ducts, etc . . . ) of the body for the purpose of maintaining the patency or state of dilation of the passageway, reinforcing the passageway, or anchoring a tubular graft or other object within the passageway.

Typically, such stents are implanted in blood vessels to maintain dilation and patency of an occluded region of blood vessel, or to bridge a weakened or aneurysmic region of blood vessel. On the other hand, some typical non-vascular applications of such stents are for the treatment of constrictions or injuries to the gastrointestinal tract (e.g., esophagus), ducts of the biliary tree (e.g., common bile duct) or anatomical passageways of the genitourinary tract (e.g., ureter, urethra fallopian tube, etc.).

Transluminally implantable stents are initially disposed in a compact configuration of relatively small diameter, and are initially mounted upon or within a delivery catheter to facilitate insertion and transluminal advancement of the stent into the desired anatomical passageway. Thereafter, such stents are radially expanded to a larger "operative" diameter which is equal to or slightly larger than the diameter of the anatomical passageway in which the stent is to be implanted. When radially expanded to such operative diameter, the stent will typically become released or separated from the delivery catheter and anchored or frictionally engaged to the surrounding wall of the anatomical passageway.

Some stents have a pliable, continuous tubular covering, in which case they are typically referred to as a "stented graft" or "stent-graft".

In general, stents and stented grafts fall into two major categories—a) self-expanding and b) pressure-expandable. Those of the self-expanding variety may be formed of resilient or shape memory material (e.g., spring steel or nitinol™) which is capable of self-expanding from its first (radially compact) diameter to its second (operative) diameter without the exertion of outwardly-directed force against the stent or stented graft. Examples of such self-expanding stents and stented grafts are set forth in U.S. Pat. Nos. 4,655,771 (Wallsten, et al); 4,954,126 (Wallsten); 5,061,275 (Wallsten, et al); 4,580,568 (Gianturco); 4,830,003 (Wolf, et al); 5,035,706 (Gianturco, et al); 5,330,400 (Song) and 5,354,308 (Simon, et al) and Foreign Patent Publication Nos. W094\12136; W092\06734 and EPA183372. Those of the pressure-expandable (i.e., "passive expandable") variety may be formed of plastically deformable material (e.g., stainless steel) which is initially formed in its first (radially compact) diameter and remains stable in such first diameter until such time outwardly directed pressure is exerted upon the stent or stented graft to cause radial expansion and resultant plastic deformation of the stent or stented graft, to its second (operative) diameter. Examples of such pressure-expandable stents and stented grafts are set forth in U.S. Pat. Nos.5,135,536 (Hillstead); 5,161,547 (Tower); 5,292,331 (Boneau); 5,304,200 (Spaulding); 4,733,665 (Palmaz); 5,282,823 (Schwartz, et al); 4,776,337 (Palmaz); and 5,403, 341 (Solar) and Foreign Patent Publication Nos. EPA480667; and W09508966.

In many applications, careful positioning and sound anchoring of the stent or stented graft is critical to the successful treatment of the underlying medical problem. In this regard, the delivery catheter which is utilized to insert and position the stent or stented graft may be an important aspect of the overall system. Various types of delivery catheters for stents and stented grafts have been previously known, including those described in U.S. Pat. Nos. 4,665, 918 (Garza, et al); 4,733,665 (Palmaz); 4,739,762 (Palmaz); 4,762,125 (Leiman, et al);,776,337 (Palmaz); 4,838,269 (Robinson, et al); 4,994,071 (MacGregor); 5,037,427 (Harada, et al); 5,089,005 (Harada); 5,102,417 (Palmaz); 5,108,416 (Ryan, et al); 5,141,498 (Christian); 5,181,920 (Mueller, et al); 5,195,984 (Schatz); 5,201,901 (Harada, et al); 5,269,763 (Boehmer, et al); 5,275,622 (Lazarus, et al); 5,290,295 (Querals, et al); 5,306,294 (Winston, et al); 5,318, 588 (Horzewski, et al); 5,344,426 (Lau, et al); 5,350,363 (Goode, et al); 5,360,401 (Turnland); 5,391,172 (Williams, et al); 5,397,345 (Lazarus); 5,405,380 (Gianotti, et al); 5,443,452 (Hart, et al); 5,453,090 (Martinez, et al); 5,456, 284 (Ryan, et al); and 5,456,694 (Marin, et al) and Foreign Patent Publication Nos. EP-0308-815-A2; EP-0335-341-A1; EP-364-787-A; EP0442-657-A2; EP-482976-A; EP-0505-686-A1; EP-0611-556-A1; EP-0638-290-A1; W094\15549; W095\01761; GB2196-857-A; DE3042-229; and DE3737-121-A.

As previously indicated, many types of stents or stented grafts are currently used in relation to the treatment of various disorders. Perhaps the most common use of radially expandable stents and stented grafts is in relation to the treatment of narrowed or constricted blood vessels. For these applications, pressure expandable stents are typically employed, with the delivery of the stent to the desired treatment site being facilitated through the use of a delivery catheter including an inflatable balloon which is used to facilitate the radial expansion of the stent positioned thereupon to its final, operative diameter.

When using pressure expandable stents or stented grafts on a delivery catheter including an inflatable balloon, the stent or stented graft must be manually mounted to the balloon of the delivery catheter by the physician prior to the initiation of the treatment. Such mounting is typically accomplished by the physician manually squeezing or compressing the stent or stented graft onto the balloon of the delivery catheter. It is also known in the prior art for delivery catheters to be provided wherein the stent or stented graft is premounted thereto. In this respect, the stent or stented graft is mounted to the delivery catheter by the manufacturer, and sold as a combined unit.

Though the above-described mounting procedure is often used, a major drawback associated therewith is that often times the stent or stented graft is not uniformly compressed onto the balloon of the delivery catheter. Indeed, the hand crimping of the stent or stented graft onto the balloon of the delivery catheter usually results in uneven crimping. Such non-uniform or uneven crimping of the stent or stented graft onto the balloon in turn results in non-uniform or uneven re-expansion of the stent or stented graft when radially expanded by the inflation of the balloon. If re-expanded in a nonuniform manner, the stent or stented graft, though being in contact with the luminal surface of a particular anatomical passageway, will not necessarily exert even pressure thereagainst, which is undesirable due to the increased risk of the stent or stented graft dislodging from its operative position within the treatment site. Additionally, such non-uniform crimping may cause problems during the advancement of the delivery catheter through the anatomical passageway to the desired treatment site. Such problems include those portions of the stent or stented graft which are not compressed against the balloon of the delivery catheter inadvertently contacting and damaging the lining of the luminal surface of the anatomical passageway.

In view of the foregoing, it is highly desirable to facilitate the uniform crimping or compression of the stent or stented graft over the balloon of the delivery catheter. The present invention addresses this need by providing an apparatus and method which, through the use of hydraulics, facilitates the uniform radial compression of the stent or stented graft about a portion of the delivery catheter. The present invention is used primarily in relation to pressure expandable stents or stented grafts which are mounted to the balloon of a delivery catheter. However, the present invention may also be used in relation to self-expanding stents or stented grafts including a latching mechanism which engages when the stent or stented graft is radially compressed.

SUMMARY OF THE INVENTION

In accordance with the present invention, there is provided an apparatus for mounting a radially expandable intraluminal stent or stented graft onto a delivery catheter. The apparatus comprises a hollow housing which defines an interior chamber and a fluid port which communicates with the interior chamber. Disposed within the interior chamber of the housing is a collapsible, resilient tubular sleeve which is sized to receive a portion of the delivery catheter having the stent or stented graft positioned thereupon. The sleeve includes an open end which communicates with the exterior of the housing. In the present apparatus, the pressurization of the interior chamber of the housing via its fluid port facilitates the uniform radial compression of the elongate sleeve, with the depressurization of the housing via its fluid port being operational to allow the sleeve to resiliently return to an uncompressed state. The collapse of the sleeve in turn facilitates the uniform radial compression or crimping of the stent or stented graft therewithin, thus mounting the stent or stented graft onto the delivery catheter. Typically, the present apparatus is used in conjunction with pressure expandable stents for mounting the same onto the radially expandable balloon of a delivery catheter.

The elongate, tubular sleeve of the present apparatus may be fabricated from polyethylene (PE) having a preferred wall thickness of from about 0.001 to 0.003 inches. The sleeve may alternatively be fabricated from polyethylene terephthalate (PET) having a preferred wall thickness of from about 0.0001 to 0.001 inches, or from nylon (PEBAX™, Atochimie, Courbevoie, Hauts-Ve-Sine, France) having a preferred wall thickness of from about 0.001 to 0.003 inches. Additionally, the sleeve may be fabricated from an elastomeric material having a preferred wall thickness of approximately 0.005 inches.

In the apparatus constructed in accordance with the present invention, the housing may further comprise a pressure gauge fluidly connected to the interior chamber for monitoring the pressure level therewithin. The interior chamber of the housing is typically pressurized with a fluid, and preferably a liquid for minimum compressibility. However, the interior chamber may alternatively be pressurized with a gas, though the use of a gas for the pressurizing medium is less desirable due to its increased compressibility as compared to a liquid. The pressurization of the interior chamber is typically facilitated by an angioplasty balloon inflation device (e.g., the syringe used to inflate the balloon of the delivery catheter). In some instances, the angioplasty balloon inflation device may include its own pressure gauge, thus eliminating the need for the optional pressure gauge fluidly connected to the interior chamber of the housing. However, those of ordinary skill in the art will recognize that alternative devices may be used to pressurize the interior chamber of the housing.

Further in accordance with the present invention, there is provided a hydraulic method of mounting a radially expandable intraluminal stent or stented graft onto a delivery catheter. The method comprises the initial step of providing a crimping apparatus which has the above-described structural and functional attributes. Thereafter, a radially expandable stent or stented graft is positioned upon a portion of the delivery catheter, with that portion of the delivery catheter having the stent or stented graft positioned thereupon then being inserted into the sleeve via the open end thereof. Thereafter, the interior chamber of the housing is pressurized via the fluid port to facilitate the uniform radial compression of the sleeve and the stent or stented graft positioned therein about the delivery catheter. The interior chamber of the housing is then depressurized via the fluid port, with the portion of the delivery catheter having the stent or stented graft mounted thereto being removed or withdrawn from within the interior of the sleeve.

As previously indicated, the interior chamber of the housing is typically pressurized with a fluid through the use of the syringe or other inflation fluid infusion device used to facilitate the inflation of the balloon of the delivery catheter. Additionally, the stent positioned upon the delivery catheter will typically comprise a pressure expandable stent, though self-expanding stents including latching mechanisms which engage when the stent is collapsed may also be used in conjunction with the present invention.

BRIEF DESCRIPTION OF THE DRAWINGS

These, as well as other features of the present invention, will become more apparent upon reference to the drawings wherein:

FIG. 1 is a perspective view of the mounting apparatus of the present invention, illustrating the manner in which a delivery catheter having an uncompressed stent positioned thereupon is inserted into the mounting apparatus;

FIG. 2 is a cross-sectional view of the mounting apparatus, illustrating the delivery catheter and uncompressed stent as positioned therein prior to the pressurization of the interior chamber thereof;

FIG. 3 is a cross-sectional view of the mounting apparatus, illustrating the delivery catheter and radially compressed stent as positioned therein subsequent to the pressurization of the interior chamber thereof;

FIG. 4 is a cross-sectional view taken along line 4—4 of FIG. 3; and

FIG. 5 is a partial perspective view of the delivery catheter, illustrating the stent as being radially compressed thereon through the use of the mounting apparatus shown in FIGS. 1–3.

DETAILED DESCRIPTION OF THE PREFERRED EMBODIMENT

Referring now to the drawings wherein the showings are for purposes of illustrating a preferred embodiment of the present invention only, and not for purposes of limiting the same, FIG. 1 perspectively illustrates an apparatus 10 for mounting a radially expandable intraluminal stent 12 or stented graft onto a delivery catheter 14. The stent 12 with which the apparatus 10 is utilized will typically comprise a pressure expandable stent, with the stent 12 shown in FIGS. 1–5 being of a type commonly referred to as a "zig-zag" stent. Additionally, the delivery catheter 14 upon which the pressure expandable stent 12 is positioned will typically comprise a balloon delivery catheter having a tubular body 16 which includes an elongate, inflatable balloon 18 attached to the outer surface thereof in relative close proximity to its distal end. The stent 12 is mounted to the balloon 18 of the delivery catheter 14 by initially positioning the stent 12 over the balloon 18, and subsequently radially compressing the stent 12 thereabout. The deployment of the collapsed stent 12 into a desired intraluminal site is facilitated by the inflation of the balloon 18, which in turn causes the stent 12 mounted thereto to be expanded radially outwardly into direct contact with the luminal surface of an anatomical passageway. As will be described in more detail below, the apparatus 10 of the present invention is specifically adapted to facilitate the mounting of the stent 12 onto the delivery catheter 14 through the uniform radial compression of the stent 12 about the balloon 18.

Those of ordinary skill in the art will recognize that the apparatus 10 of the present invention may also be used to facilitate the mounting of other types of pressure expandable stents or stented grafts onto the balloon 18 of the delivery catheter 14. Additionally, the apparatus 10 may be used to facilitate the mounting of self-expanding stents or stented grafts onto the balloon 18 of the delivery catheter 14 wherein such self-expanding stents or stented grafts include latching mechanisms which engage when the stent or stented graft is collapsed. Moreover, the apparatus 10 may be used to facilitate the mounting of stents or stented grafts onto delivery catheters other than for balloon delivery catheters. Thus, the particular descriptions of the stent 12 and delivery catheter 14 set forth herein are for illustrative purposes only and are not intended to limit the scope of the present invention.

In the preferred embodiment, the apparatus 10 comprises a hollow, cylindrically configured housing 20 which defines a proximal end 22 and a distal end 24. The distal end 24 of the housing 20 may be enclosed by an end cap 26 which, though not shown, may comprise an integral portion of the housing 20. Disposed within the proximal end 22 of the housing 20 is an annular entry member 28 which defines a circularly configured opening 30 extending axially therethrough. The housing 20, end cap 26 and entry member 28, and more particularly the inner surfaces thereof, collectively define an interior chamber 32 of the housing 20.

As best seen in FIGS. 2 and 3, disposed within the interior chamber 32 of the housing 20 is a collapsible, resilient tubular sleeve 34 having a proximal end which is attached to the inner surface of the entry member 28 and a distal end which is attached to the inner surface of the end cap 26. When attached to the entry member 28, the proximal end of the sleeve 34 circumvents the opening 30, with the inner surface of the sleeve 34 being substantially continuous with the peripheral inner wall of the entry member 28 which defines the opening 30. When attached to the end cap 26 and entry member 28 in the aforementioned manner, the sleeve 34 extends axially through the interior chamber 32, with the interior of the sleeve 34 communicating with the exterior of the apparatus 10 via the opening 30 within the entry member 28.

The sleeve 34 of the apparatus 10 may be fabricated from polyethylene (PE) having a preferred wall thickness of from about 0.001 to 0.003 inches. The sleeve 34 may alternatively be fabricated from polyethylene terephthlate (PET) having a preferred wall thickness of from about 0.0001 to 0.001 inches, or from nylon (PEBAX™, Atochimie, Courbevoie, Hauts-Ve-Sine France) having a preferred wall thickness of from about 0.001 to 0.003 inches. Additionally, the sleeve 34 may be fabricated from an elastomeric material having a preferred wall thickness of approximately 0.005 inches. In all embodiments, the sleeve 34 is sufficiently resilient to be selectively collapsible and expandable in accordance with changes in the pressure level within the interior chamber 32, as will be discussed in more detail below.

As seen in FIGS. 1–3, the apparatus 10 constructed in accordance with the present invention further comprises a fluid port 36 which is attached to the housing 20 and communicates with the interior chamber 32 thereof. Also attached to the housing 20 adjacent the fluid port 36 is a pressure gauge 38 which also communicates with the interior chamber 32.

Having thus described the structural components of the apparatus 10, the method of using the same to facilitate the mounting of the stent 12 upon the balloon 18 of the delivery catheter 14 will now be described with reference to FIGS. 1–5.

In the present method, the stent 12, while in its uncollapsed state, is centrally positioned upon the balloon 18 of the delivery catheter 14 such that the opposed ends of the balloon 18 protrude from respective ends of the stent 12. Thereafter, as seen in FIG. 2, the delivery catheter 14 having the stent 12 positioned upon the balloon 18 is inserted into the interior of sleeve 34 via the opening 30 within the entry member 28. Importantly, the inner diameter of the sleeve 34 is sized so as to allow the uncollapsed stent 12 to be easily inserted into the sleeve 34 without interfering with the inner surface thereof.

Subsequent to the insertion of the delivery catheter 14 and stent 12 into the sleeve 34 in the manner shown in FIG. 2, the interior chamber 32 of the housing 20 is pressurized via the fluid port 36. More particularly, the interior chamber 32 is pressurized with a fluid, with such pressurization typically being facilitated by an angioplasty balloon inflation device (e.g., the syringe used to inflate the balloon 18 of the delivery catheter 14). However, those of ordinary skill in the art will recognize that alternative devices may be used to pressurize the interior chamber 32 of the housing 20. As seen in FIG. 3, due to the resiliency of the sleeve 34, the pressurization of the interior chamber 32 in the aforementioned manner facilitates the uniform radial compression of the sleeve 34 about the stent 12 positioned therewithin. The application of the uniform radial compressive forces to the stent 12 by the sleeve 34 in turn causes the stent 12 to be uniformly radially collapsed or compressed about (i.e., mounted to) the balloon 18 of the delivery catheter 14.

After the stent 12 has been mounted to the balloon 18 of the delivery catheter 14 in the aforementioned manner, the interior chamber 32 of the housing 20 is depressurized via the fluid port 36. The resultant return of the interior chamber 32 to atmospheric pressure causes the sleeve 34 to resiliently return to its original, uncompressed configuration as shown in FIG. 2. Thereafter, the delivery catheter 14 having the stent 12 mounted thereto is removed from within the sleeve 34 via the opening 30, with the stent 12 being tightly collapsed onto the balloon 18 of the delivery catheter 14 in the manner shown in FIG. 5.

The optional inclusion of the pressure gauge 38 with the apparatus 10 provides a visual indication as to whether the pressure level within the interior chamber 32 is sufficient to facilitate the uniform radial compression of the sleeve 34 from its uncollapsed state (shown in FIG. 2) to its collapsed state (shown in FIG. 3). It will be recognized that an additional or alternative visual indication of the sleeve 34 moving to its collapsed state may be achieved by fabricating the housing 12 from a transparent or translucent material.

Advantageously, the apparatus 10 constructed in accordance with the present invention facilitates the uniform crimping or compression of the stent 12 or stented graft over the balloon 18 of the delivery catheter 14. Due to such uniform compression, the stent 12 radially expands in a uniform manner upon the inflation of the balloon 18 and thus exerts even pressure against the luminal surface of the anatomical passageway when placed into direct contact wherewith. As such, the stent 12, when in its operative position within the anatomical passageway, is less susceptible to dislodging within the treatment site. Additionally, the uniform compression of the stent 12 about the balloon 18 substantially decreases the risk of the stent 12 inadvertently contacting and damaging the lining of the luminal surface of the anatomical passageway during the advancement of the delivery catheter 14 to the desired treatment site.

Additional modifications and improvements of the present invention may also be apparent to those of ordinary skill in the art. Thus, the particular combination of parts described and illustrated herein is intended to represent only one embodiment of the present invention, and is not intended to serve as limitations of alternative devices within the spirit and scope of the invention.

What is claimed is:

1. A method of mounting a radially expandable intraluminal stent onto a delivery catheter, said method comprising the steps of:
   (a) providing a stent mounting apparatus which comprises:
      (1) a hollow housing defining an interior chamber which is filled with a fluid; and
      (2) a collapsible, resilient tubular sleeve disposed within the interior chamber of the housing, said sleeve having an open end which communicates with the exterior of the housing;
   (b) positioning the radially expandable stent upon a portion of the delivery catheter;
   (c) inserting the portion of the delivery catheter having the stent positioned thereupon into the sleeve; and
   (d) pressurizing the fluid within the interior chamber of the housing to facilitate the uniform radial compression of the sleeve and the stent positioned therein about the delivery catheter.

2. The method of claim 1 further comprising the steps of:
   (e) depressurizing the interior chamber of the housing; and
   (f) removing the portion of the delivery catheter having the stent mounted thereto from within the sleeve.

3. The method of claim 1 wherein step (b) comprises positioning a pressure expandable stent onto the delivery catheter.

4. The method of claim 1 wherein step (d) comprises pressurizing the interior chamber of the housing with a liquid.

5. The method of claim 1 wherein step (d) comprises pressurizing the interior chamber of the housing with a gas.

6. A system for installing a radially expandable intraluminal prosthesis within a body lumen wherein the system comprises an elongate, pliable delivery catheter having a radial expansion member formed thereon, and a radially expandable prosthesis mounted upon said radial expansion member in a radially compact configuration such that subsequent expansion of the expansion member will cause the prosthesis to become radially expanded, wherein said prosthesis has been mounted upon said delivery catheter by the method which comprises the steps of:
   (a) providing a stent mounting apparatus which comprises:
      (1) a hollow housing defining an interior chamber which is filled with a fluid;
      (2) a collapsible, resilient tubular sleeve disposed within the interior chamber of the housing, said sleeve having an open end which communicates with the exterior of the housing;
   (b) positioning the radially expandable stent upon a portion of the delivery catheter;
   (c) inserting the portion of the delivery catheter having the stent positioned thereupon into the sleeve; and
   (d) pressurizing the fluid within the interior chamber of the housing to facilitate the uniform radial compression of the sleeve and the stent positioned therein about the delivery catheter.

7. The method of claim 6 wherein the radially expandable prosthesis is a stent.

8. The method of claim 7 wherein the radially expandable prosthesis is a stent formed of plastically deformable material.

9. The method of claim 7 wherein the radially expandable prosthesis is a stent having a ratchet mechanism which enables the stent to be radially expanded by exertion of outward radial pressure against the stent.

10. The method of claim 6 wherein the radially expandable prosthesis is a stented graft.

11. The method of claim 10 wherein the stented graft is a tubular graft having at least one radially expandable stent member attached thereto.

* * * * *